(12) United States Patent
Zahn

(10) Patent No.: US 9,724,859 B2
(45) Date of Patent: Aug. 8, 2017

(54) METHOD OF PRODUCING A SYRINGE BARREL FOR MEDICAL PURPOSES

(71) Applicant: Schöttli AG, Diessenhofen (CH)

(72) Inventor: Lothar Zahn, Gailingen (DE)

(73) Assignee: HUSKY INJECTION MOLDING SYSTEMS LTD., Bolton, Ontario (CA)

( * ) Notice: Subject to any disclaimer, the term of this patent is extended or adjusted under 35 U.S.C. 154(b) by 252 days.

(21) Appl. No.: 14/399,258

(22) PCT Filed: May 14, 2013

(86) PCT No.: PCT/CH2013/000082
§ 371 (c)(1),
(2) Date: Nov. 6, 2014

(87) PCT Pub. No.: WO2013/170393
PCT Pub. Date: Nov. 21, 2013

(65) Prior Publication Data
US 2015/0123311 A1    May 7, 2015

(30) Foreign Application Priority Data
May 14, 2012  (CH) ........................................ 676/012

(51) Int. Cl.
B29C 45/14      (2006.01)
A61M 5/34       (2006.01)
B29C 45/26      (2006.01)
B29L 31/00      (2006.01)

(52) U.S. Cl.
CPC ....... *B29C 45/14008* (2013.01); *A61M 5/343* (2013.01); *B29C 45/14065* (2013.01); *B29C 45/14262* (2013.01); *B29C 45/14336* (2013.01); *B29C 45/14598* (2013.01); *B29C 45/261* (2013.01); *A61M 2207/00* (2013.01); *A61M 2207/10* (2013.01); *B29C 2045/14131* (2013.01); *B29C 2045/14139* (2013.01); *B29L 2031/7544* (2013.01)

(58) Field of Classification Search
None
See application file for complete search history.

(56) References Cited

U.S. PATENT DOCUMENTS

| 3,330,004 | A |   | 7/1967  | Cloyd et al. |
| 3,402,713 | A | * | 9/1968  | Senkowski ........... A61M 5/178 264/318 |
| 4,354,495 | A | * | 10/1982 | Bodicky ........... A61M 25/0014 264/127 |
| 5,693,026 | A | * | 12/1997 | Spinello .................. A61L 11/00 264/525 |

(Continued)

FOREIGN PATENT DOCUMENTS

| EP | 2140896 A1    | 1/2010 |
| WO | 2012003221 A1 | 1/2012 |
| WO | 2012043544 A1 | 4/2012 |

OTHER PUBLICATIONS

PCT International Search Report; Schultz, Ottmar; 4 pages, Aug. 15, 2013.

*Primary Examiner* — Edmund Lee

(57) ABSTRACT

The equipping of syringe barrels (11) with needles (25) takes place before the injection of the plastic, in which the needles (25) are introduced through the fixed part (5) of the injection mold (1) by a suitable transport device (transport rollers 33).

8 Claims, 2 Drawing Sheets

(56) References Cited

U.S. PATENT DOCUMENTS

Figure 1:
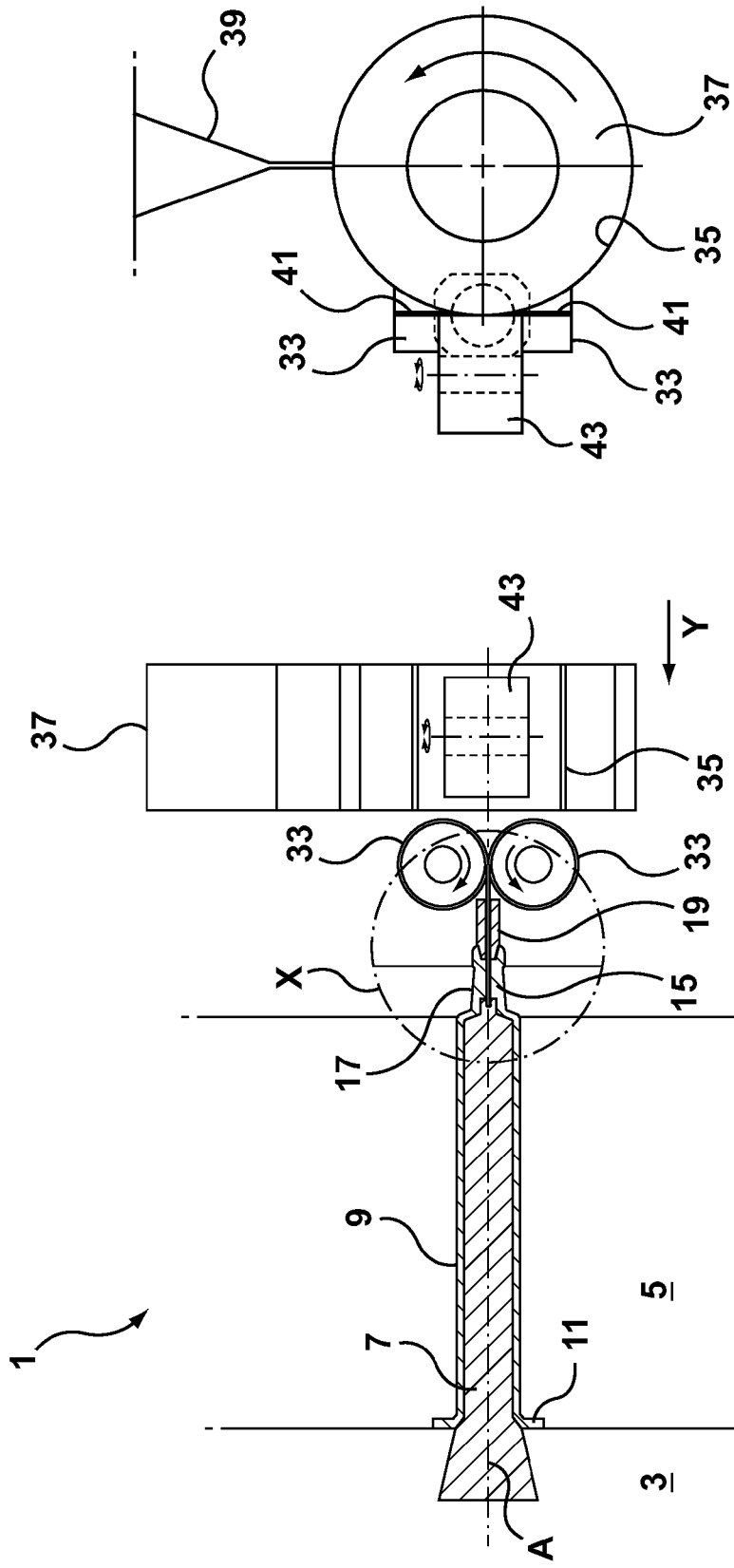

| | | | | |
|---|---|---|---|---|
| 8,496,862 B2* | 7/2013 | Zelkovich | ............. | A61M 5/343 |
| | | | | 264/259 |
| 2010/0145284 A1* | 6/2010 | Togashi | ............ | B29C 45/14065 |
| | | | | 604/218 |
| 2010/0270702 A1 | 10/2010 | Zelkovich et al. | | |
| 2012/0010573 A1 | 1/2012 | Lundquist | | |
| 2013/0138047 A1* | 5/2013 | Takemoto | ............. | A61M 5/343 |
| | | | | 604/192 |

* cited by examiner

… (1) …

METHOD OF PRODUCING A SYRINGE BARREL FOR MEDICAL PURPOSES

TECHNICAL FIELD

The object of the invention is a method for producing a syringe barrel according to the preamble of claim 1.

The invention further relates to a device for carrying out the method according to the preamble of claim 5.

BACKGROUND

Syringes for medical purposes comprise a syringe barrel, at the front end of which is arranged a needle and a piston, which is pulled up with the medium to be injected on the one hand and is later injected. In most cases, the needle is supplied packed separately from the syringe or from the syringe barrel and piston. However, it is also known, in particular for syringes for injections of inoculants and the like, to manufacture this with the needle already attached. In the manufacture of such syringes, the needle pointed at the front end in the case of an open mold with a handling unit is led through the cavity into the injection mold and then partially enclosed by the liquid plastic in the injection process. To insert the needle through the open mold it is necessary to configure the needles in an appropriate manner, so that they can be detected by the handling unit and then led between the open mold in the cavity. This leads to a reduction of cycles per unit of time and consequently higher production costs.

Further, a medical syringe with integrated needle is known from WO 2012/003221 A1. The needle is held positioned with clamping jaws during the injection process in such a way that the end opposite the sharpened end of the needle definitely does not protrude beyond the inner wall of the syringe barrel. Preferably, the inner end of the needle is even held slightly recessed, so that even in the event of a possible shrinking of the plastic of the syringe barrel the end does not project into the interior space and therefore does not hinder the full expression of the injection liquid. In addition, the bore of the needle is held closed during the injection process by a thread or wire (strand), to prevent the penetration of plastic into the needle. The manufacture of such a syringe barrel with an integrated needle is very costly.

SUMMARY

An object of the present invention is now to optimize the delivery of the needle to the injection mold in such a way that the time period in which the fixed and the movable mold part are moved apart can be reduced.

This object is achieved by a method according to the features of claim 1 and by a device according to the features of claim 5.

The displacement of the delivery point to the back of the fixed mold part allows the two mold parts of the injection mold to close again immediately directly after the ejection of the freshly injected molded part, here a syringe barrel, together with the inserted needle, and simultaneously to introduce the next needle far enough into the cavity so that its rear end can be insert-molded. The rear end of the needle is in this case retracted into a precision bore in the core of the syringe barrel and thereby the bore in the needle is sealingly enclosed, so that no plastic can penetrate. The guiding of the needle into the cavity of the syringe barrel and the bore in the core from outside the mold through the fixed mold has the further advantage that the needle does not advance to the tip end, but is slid into the blunt rear end and the end with the sharpened tip can not be infringed upon during the sliding in. A further advantage is that the separation of the needles can be carried out easily and no complicated handling systems and also no configuration of the needles are necessary.

DETAILED DESCRIPTION OF THE DRAWINGS

The invention is explained in more detail with reference to an illustrated embodiment.

Figure 2:
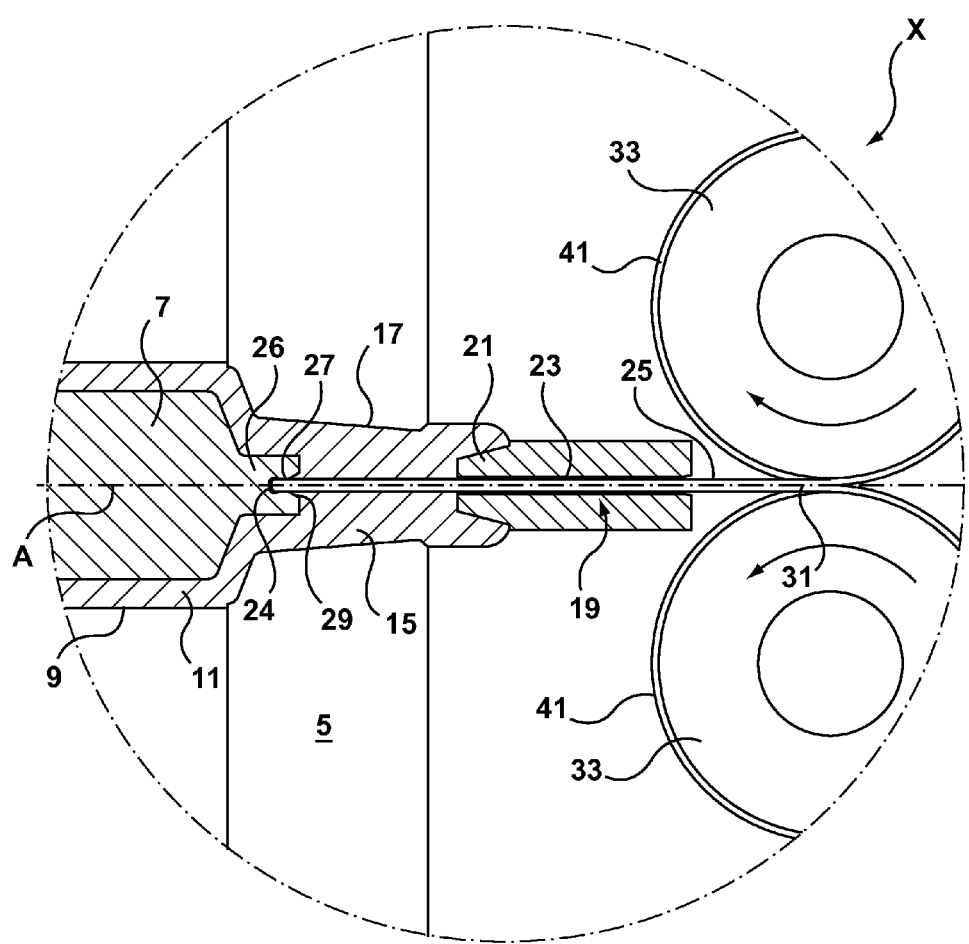

FIG. 1 shows schematically a vertical section through the two mold halves and a device for feeding and introducing the needles, FIG. 2 shows an expanded illustration of the region X in FIG. 1 and FIG. 3 shows a view of the separating and feed device from the direction of the arrow Y in FIG. 1.

DETAILED DESCRIPTION OF THE NON-LIMITING EMBODIMENT(S)

Reference numeral 3 represents schematically the movable part of an injection mold 1 and reference numeral 5 represents the fixed part of an injection mold 1. On movable part 3 of the injection mold 1 a core 7 is attached, which protrudes into the cavity 9 of a syringe barrel 11 in the fixed mold part 5. Then in the cylindrical cavity 9 on the right side in the figures a tapered cavity section 17, for example, forming the needle intake 15 is visible. A needle guide tube 19 with a frustoconical end 21 protrudes into the end of the cavity section 17. An axial bore 23 in the guide tube 19 has a diameter which can lead the rear end 24 of a needle 25 substantially without clearance and sealingly during the injection.

At the free end 26 of the core 7 a blind hole 27 is formed, which on the input side preferably comprises a conical inlet region 29.

The front end 31 of the needle 25 provided with a tip is held by two transport rollers 33. On the periphery of a feed drum 37 a plurality of grooves 35 are embedded spaced apart, in which individual needles 25 can be fed to the transport rollers 33 by a feed hopper 39 or another suitable separating device.

The transfer of the needles 17 from the grooves 35 in the feed drum 37 between the two transport rollers 33, or in slots 41 applied to its periphery, takes place using a friction roller 43, which with its rubberized surface leads out the needles 25 axially from the grooves 35 on the feed drum 37.

The method and the device are explained briefly below. After the opening of the two injection mold halves 3, 5 by driving away the movable part 3 from the fixed part 5 and ejection of a syringe barrel 11 finished and provided with an injected needle 17 the injection mold 1 is immediately closed again, that is, the movable mold part 3 is re-introduced to the fixed mold part 5. Simultaneously, afterwards or shortly beforehand a needle 25 is slid from a groove 35 on the feed drum 37 between the transport rollers 33 by the friction roller 43 or in the slots 41 on the transport rollers 33 and advanced by the rotating transport rollers 33 in axial direction A through the bore 23 in the guide tube 19 in the blind hole 27 at the front end of the core 7 until it stops. The needle 25 is held axially pressed by the transport rollers 33 in the blind hole 27, until the cavity 9, in which the syringe barrel 11 is formed, is completely filled with plastic. The holding of the needle 25 during the injection of the plastic can—as described—take place through the torque of the transport rollers 33 or also through another device (not shown) pressing the needle 25 into the blind hole 27, if the loading of the injection mold 1 takes place through another device than that described here.

After completion of the injection process and the necessary crystallization and cooling time for the plastic the syringe barrel 11 can be ejected with the now molded needle 25 by opening the two mold parts 3 and 5 and then immediately closed again, while after the ejection of the syringe barrel 11 a new needle 25 is already inserted through the guide tube 19 in the fixed part 5 in the cavity 9 of the syringe barrel 11.

The device for feeding the needles 25 has a very simple structure, since the needles 25 drop from the feed hopper 39, by gravity for example, into the grooves 35 on the feed drum 37 and can then be fed by the friction roller 43 to the transport rollers 33. The positioning of the needle 25 takes place forcibly with the guide tube 19 and the sealing of the bore in the needle through the blind hole 27, which sealingly encloses the end of the needle 25.

The invention claimed is:

1. Method for producing a syringe barrel with an inserted needle for medical purposes, comprising:
    inserting a needle into a cavity of an injection mold prior to injection of plastic wherein the needle is inserted by a rear end thereof into the cavity from outside the injection mold from the rear through a guide tube in a fixed part of the injection mold;
    holding the needle at its front end in a region of a point of the needle during an injection cycle by a force acting in the direction of insertion;
    filling the cavity with injection of plastic therein to form a syringe barrel with the needle;
    ejecting of the syringe barrel together with the insert molded needle; and
    inserting another needle from outside the injection mold from the rear through the guide tube during or after the ejection.

2. Method according to claim 1, wherein with closing of the injection mold the needle is already introduced therein.

3. Method according to claim 1, further comprising transport means performing at least one of releasing the needle at the end of an injection cycle from a holding and clamping position and pushing the needle further forward from the fixed part during the ejection.

4. Apparatus for producing a syringe barrel with an inserted needle for medical purposes, comprising an injection mold having a moveable part and a fixed part, and a transport means arranged behind the fixed part, the transport means configured to insert individual needles into a cavity defined between the moveable and fixed parts of the injection mold through a guide tube in the fixed part.

5. Apparatus according to claim 4, wherein the moveable part includes a core for molding the syringe barrel, a blind hole is formed at a free end of the core for guiding and receiving the rear end of the needle.

6. Apparatus according to claim 5, wherein the blind hole is dimensioned such that the rear end of the needle is tightly enclosed.

7. Method according to claim 1, wherein inserting of the needle includes a sliding thereof through the guide tube in the fixed part of the injection mold by a transport means that is arranged behind the fixed part of the injection mold, wherein the rear end of the needle is introduced into a blind hole at the front end of a core, which is held on a movable part of the injection mold, and is retained therein by the transport means.

8. Method according to claim 7, wherein the transport means performs at least one of releasing the needle at the end of the injection cycle from a holding and clamping position and pushing the needle further forward from the fixed part during the ejection.

* * * * *